United States Patent
Denny et al.

(10) Patent No.: US 7,235,578 B2
(45) Date of Patent: Jun. 26, 2007

(54) PROCESSES FOR PREPARING 3-SUBSTITUTED 1-(CHLOROMETHYL)-1,2-DIHYDRO-3H-[RING FUSED INDOL-5-YL-(AMINE-DERIVED)] COMPOUNDS AND ANALOGUES THEREOF, AND TO PRODUCTS OBTAINED THEREFROM

(75) Inventors: William Alexander Denny, Auckland (NZ); Shanjin Yang, Auckland (NZ); Graham John Atwell, Auckland (NZ); Scott Charles Jeffrey, Everett, WA (US)

(73) Assignee: Auckland Uniservices Limited, Auckland (NZ)

( * ) Notice: Subject to any disclaimer, the term of this patent is extended or adjusted under 35 U.S.C. 154(b) by 45 days.

(21) Appl. No.: 10/514,893

(22) PCT Filed: May 19, 2003

(86) PCT No.: PCT/NZ03/00094

§ 371 (c)(1),
(2), (4) Date: Nov. 17, 2004

(87) PCT Pub. No.: WO03/097635

PCT Pub. Date: Nov. 27, 2003

(65) Prior Publication Data
US 2005/0148651 A1    Jul. 7, 2005

(30) Foreign Application Priority Data
May 17, 2002   (NZ) ..................................... 519031

(51) Int. Cl.
*A61K 31/403*   (2006.01)
*C07D 209/60*   (2006.01)

(52) U.S. Cl. ..................................... 514/411; 548/427
(58) Field of Classification Search ................ 514/411; 548/427
See application file for complete search history.

(56) References Cited

OTHER PUBLICATIONS

Atwell, G., et al; "Synthesis and Cytotoxicity of 5-Amino-1-(chloromethyl)-3-[(5,6,7-trimethoxyindol-2-yl)carbonyl]-1,2-dihydro-3H-benz[e]indole (Amino-*seco*-CNI-TMI) and Related 5-Alkylamino Analogues: New DNA Minor Groove Alkylating Agents"; *J. Org. Chem.*; vol. 63, pp. 9414-9420 (1998).

Tercel, M., et al; "Synthesis and Cytotoxicity of Amino-*seco*-DSA: An Amino Analogue of the DNA Alkylating Agent Duocarmycin SA"; *J. Org. Chem.*; vol. 64; pp. 5946-5953 (1999).

*Primary Examiner*—Joseph K. McKane
*Assistant Examiner*—Jason M. Nolan
(74) *Attorney, Agent, or Firm*—Nixon & Vanderhye

(57) ABSTRACT

The invention provides processes of preparing 3-substituted 1-(chloromethyl)- 1,2-dihydro-3H-[ring fused indol-5-yl (amine-derived)] compounds of formula (I) and its analogues, or a physiologically functional derivative thereof, (I), wherein A and B together may represent a fused optionally substituted benzene, naphthalene, pyridine, furan or a pyrrole ring, where the optional substituents are represented by Y; X is halogen or $OSO_2R$, and W is selected from $NO_2$, NHOH, $N(R^3)_2NHR^3$, $NHCO_2R^3$, N(phthaloyl) or $NH_2$, or W is further selected from the group (a), wherein J is selected from OH or H, and P is a group which is a substrate suitable for a nitroreductase or carboxypeptidase enzyme. The invention is also directed to the use of compounds of formula (I) prepared by the processes of the invention as cytotoxins for cancer therapy and as prodrugs for gene-directed enzyme-prodrug therapy (GDEPT) and antibody-directed enzyme-prodrug theraphy (ADEPT).

8 Claims, No Drawings

PROCESSES FOR PREPARING 3-SUBSTITUTED 1-(CHLOROMETHYL)-1,2-DIHYDRO-3H-[RING FUSED INDOL-5-YL-(AMINE-DERIVED)] COMPOUNDS AND ANALOGUES THEREOF, AND TO PRODUCTS OBTAINED THEREFROM

This application is the U.S. National Phase of International Application PCT/NZ03/00094, filed 19 May 2003, which designated the U.S. PCT/NZ03/00094 claims priority to New Zealand Application No. 519031 filed 17 May 2002. The entire content of these applications are incorporated herein by reference.

The present invention relates generally to processes of preparing 3-substituted 1-(chloromethyl)-1,2-dihydro-3H-[ring fused indol-5-yl(amine-derived)] compounds and analogues, particularly analogues substituted in the ring fused to the indole system, and the use of these compounds prepared from these processes as cytotoxins for cancer therapy and as prodrugs for gene-directed enzyme-prodrug therapy (GDEPT) and antibody-directed enzyme-prodrug therapy (ADEPT).

BACKGROUND TO THE INVENTION 5-hydroxy and 5-amino-1,2-dihydro-3H-benzo[e]indoles are known to be very potent cytotoxins. Examples of these compounds are illustrated below as the 5-hydroxy compound A; (Boger & Johnson, *Angew. Chem. Int. Ed. Engl.*, 1996, 35, 1438) and the 5-amino compound B; (Atwell et al., *J. Org. Chem.*, 1998, 63, 9414).

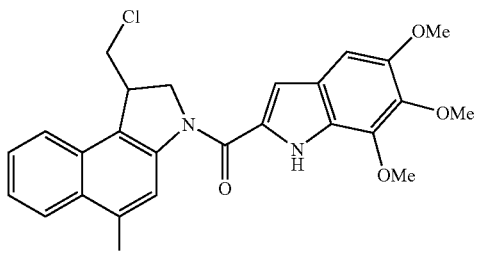

A: R = OH
B: R = NH$_2$

These compounds have IC$_{50}$s in cell culture in the low nM range. It has also been shown that both the 5-hydroxy- (Boger et al., *Tetrahedion*, 1991, 47, 2661) and the 5-amino (Gieseg et al., *AntiCancer Drug Design*, 1999, 14, 77) compounds bind in the minor groove of DNA and alkylate at the N3 of adenine in a highly regio- and sequence-selective manner. A number of analogues of the 5-hydroxy compounds have been reported in the literature, where the 5-hydroxy group has been protected as a carbamate. For potency to be expressed the carbamate is cleaved by rapid and non-specific specific enzymatic hydrolysis releasing the corresponding phenol. These compounds include carzelesin (C; Li et al., *Cancer Res.*, 1992, 52, 4904)

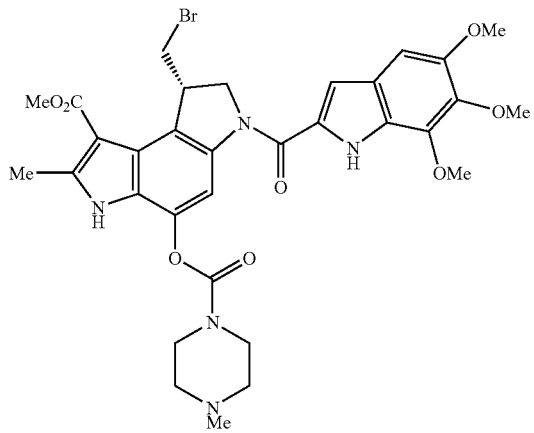

and KW-2189 (D; Kobayashi et al., *Cancer Res.*, 1994, 54, 2404).

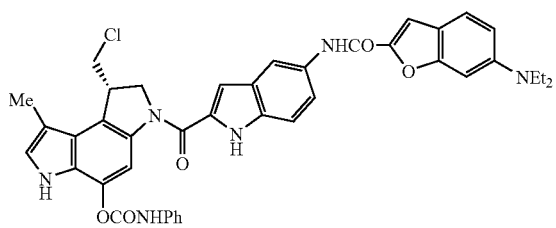

The lability of these carbamates in plasma would be desirable for systemic release of a drug. However, in contrast to the rapid and non-specific cleavage of these carbamates, the corresponding carbamates of the 5-amino chloromethyl benzoindoles (CBIs) such as for example compound E; (Hay et al., *Bioorg. Med. Chem. Lett.*, 1999, 15; 2237)

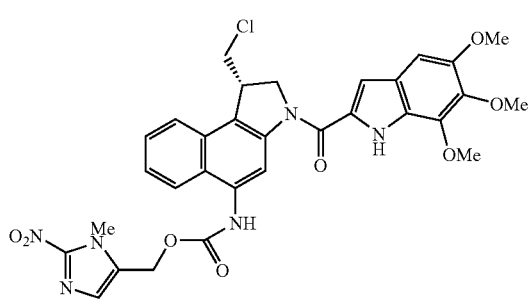

have been found to be stable and relatively non-toxic until the nitro group is reduced by a localized enzymatic-activated step that causes the fragmentation of the cytotoxic 5-aminoCBI. The minor aerobic nitroreductase (NTR) from *E. coli* (Parkinson et al., *J. Med. Chem.*, 2000, 43, 3624) might for example be used for the enzymatic-activated step. The 5-amino compounds are thus of interest as potent cytotoxins (Atwell et al., *J. Med. Chem.*, 1999, 42, 3400), and also for the formation of prodrugs for GDEPT (Hay et al., *Bioorg. Med. Chem. Lett.*, 1999, 15, 2237).

The reported (Atwell et al., *J Org Chem.*, 1998, 63, 9414) 15-step synthesis of the 5-amino compounds is from 1-hydroxynaphthalene-2-carboxylic acid, employing a nitro group as a protecting group for the eventual 5-amino group and gives the 5-amino compound B in only a 3% overall yield. The synthetic scheme is not straightforward and includes some difficult synthetic steps.

It is therefore an object of the invention to provide a synthetic method that provides better yields for these 5-aminoCBI compounds, or to at least provide the public with a useful alternative.

SUMMARY OF THE INVENTION

The present invention provides in a first aspect a method of preparing a compound of formula (I)

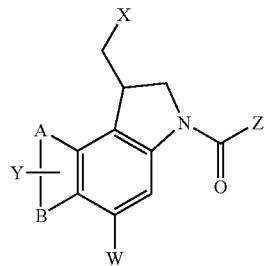

(I)

wherein
A and B together may represent a fused optionally substituted benzene, a fused optionally substituted naphthalene, a fused optionally substituted pyridine, a fused optionally substituted furan or a fused optionally substituted pyrrole ring, where the optional substituents are represented by Y; wherein
Y is selected from one or more of H, a halogen, $CH_3$, $OR^1$, $SR^1$, $NR^1R^2$, $SO_2R^1$, $CONHR^1$, CN or $CO_2R^1$ where $R^1$ or $R^2$ each independently represents H, lower $C_{1-4}$alkyl or a benzene ring, optionally substituted with one or more hydroxyl, $NO_2$ or amino groups, the amino groups being further optionally substituted with one or two $C_1$–$C_4$ alkyl groups,
X is halogen or $OSO_2R$, where R represents H, lower $C_{1-4}$alkyl or a benzene ring, optionally substituted with one or more hydroxyl, $NO_2$ or amino groups, the amino groups being further optionally substituted with one or two $C_1$–$C_4$ alkyl groups,
W is selected from $NO_2$, NHOH, $N(R^3)_2$ $NHR^3$, $NHCO_2R^3$, N(phthaloyl) or $NH_2$, where each $R^3$ is selected from a $C_{1-4}$ alkyl group optionally substituted with one or more hydroxyl or amino groups, each amino group being optionally substituted with one or two $C_{1-4}$ alkyl groups; a $C_{1-4}$ alkene group optionally substituted with hydroxyl or amino groups, each amino group being optionally substituted with one or two $C_{1-4}$ alkyl groups; or a benzene ring, optionally substituted with one or more hydroxyl, $NO_2$ or amino groups, the amino groups being further optionally substituted with one or two $C_1$–$C_4$ alkyl groups, or W is further selected from the group

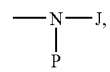

wherein J is selected from OH or R wherein R represents H, lower $C_{1-4}$alkyl or a benzene ring, optionally substituted with one or more hydroxyl, $NO_2$ or amino groups, the amino groups being further optionally substituted with one or two $C_1$–$C_4$ alkyl groups, and
P is a group which is a substrate suitable for a nitroreductase or carboxypeptidase enzyme such that one of said enzymes is able to bring about the removal of the group P which is selected from the following moieties:

| | |
|---|---|
| —C(O)—$(CZ'_2)_n$—Ph | (IIa) |
| —C(O)—O—$CH_2$—Ph | (IIb) |
| —C(O)—NH—C(COOH)—$(CH_2)_2$—COOH | (IIc) |
| —C(O)—O—$CH_2$-Phe-L-C(O)—NH—C(COOH)—$CH_2$—COOH | (IId) |
| —C(O)—O—$CH_2$-MDZ | (IIe) |
| —C(O)—O—$CH_2$-Furyl | (IIf) |
| —C(O)—O—$CH_2$-Thienyl | (IIg) |
| —C(O)—O—$CH_2$-Pyrrolyl | (IIh) | wherein each occurrence of Z' is independently H or $CH_3$, n is 1 or 2, Ph is a phenyl moiety substituted in the moiety of (IIa) by a nitro group at the 2-position, and substituted in the moiety of (IIb) by a nitro group in the 2- or 4-position, IMDZ is an imidazolyl moiety substituted in the moiety of (IIe) by a nitro group in the 2-, 4- or 5-position, and optionally further substituted by —$CH_3$ or $C_1$–$C_4$alkyl at the 1-position, wherein said alkyl is further substituted by OH, Phe is a phenylene ($C_6H_4$) ring in which the group -L, which may represent O or NH, is para to the group —$OCH_2$, wherein the Furyl, Thienyl, and Pyrrolyl groups in moieties, (IIf), (IIg) and (IIh) respectively are optionally substituted by a nitro group, wherein the Pyrrolyl group of (IIh) is further optionally substituted at the 1-position by $CH_3$ and/or $CO_2CH_2CH_3$ at the 2-position, the groups Ph and Phe, being further optionally substituted by a group $R^1$ which is a group selected from R, CONHR, NHCOR, NHR, OR or $SO_2R$ where R represents H, lower $C_{1-4}$alkyl optionally substituted by morpholino, or a benzene ring, optionally substituted with one or more hydroxyl, $NO_2$ or amino groups, the amino groups being further optionally substituted with one or two $C_1$–$C_4$ alkyl groups Z is selected from the following structures (Ia, Ib, Ic or Id)

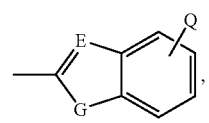

Ia

-continued

Ib

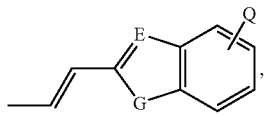

Ic

Id wherein E is selected from —N═, or —CH═,
G is O, S, or NH,
Q is either
(a) absent or independently selected from one to three of R, —OR, halogen, —NRR, —NO₂, —COOR, —CONRR, —NRCOR, OP(O)(OH)₂, O(CH₂)ₙP(O)(OH)₂, (CH₂)ₙOP(O)(OH)2, or a fused group;
where R represents H, lower C₁₋₄alkyl or a benzene ring, optionally substituted with one or more hydroxyl or amino groups, each amino group being optionally substituted with one or two C₁–C₄ alkyl groups and where n represents 1, 2 or 3; or
(b) is an additional group of formulae (Ia, Ib, Ic or Id); and
HET may represent a 5- or 6-membered carbocycle or heterocycle containing one or two atoms independently selected from N, O and S;
or a physiologically functional derivative thereof,
wherein the process for preparing a compound of formula I includes the steps of
(a) converting the NO₂ groups of a compound of formula (I') into NHBOC groups of a compound of formula (II')

I'

R' = OH
R' = OTf
R' = Halogen

II'

R'' = H
R'' = Halogen wherein the variables A, B, and Y are as defined above,
(b) converting a compound of formula (II') by allylation of the NHBOC groups into a compound of formula (III')

II''

4: R'' = H
5: R'' = Halogen

III' wherein the variables A, B, and Y are as defined above,
(c) converting a compound of formula (III') into an indole derivative of formula (IV')

III'

IV' wherein the variables A, B, and Y are as defined above, (d) reacting the compound of Formula (IV') in the presence of Zn powder to give a compound of Formula. (V')

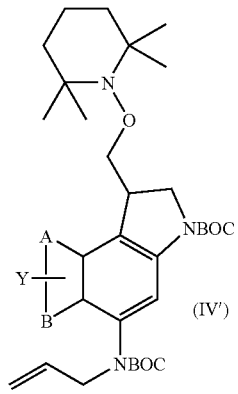

wherein the variables A, B, and Y are as defined above, and (e) reacting the NBOC and allyl groups of Formula (V') as desired to give a compound of Formula (I)

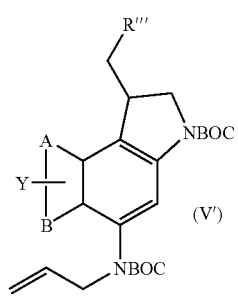

wherein the variables A, B, Y, W, and Z are as defined above.

In the process defined above, preferably A—B represent a fused benzo group. It is also preferred that X represents chloro.

More preferably, Z represents one of following groups:

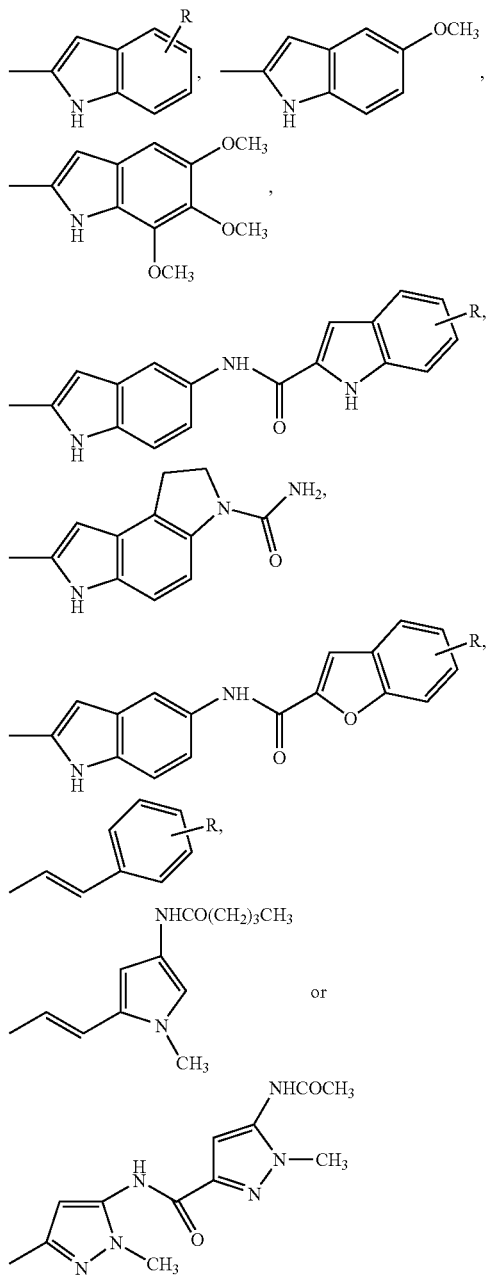

wherein the substituent —R may represent one or more substituents selected from —H, —OH, halogen, —NO$_2$, —NH$_2$, —N(C$_{1-4}$alkyl), —C$_{1-4}$alkyl, —COOC$_{1-4}$alkyl —OC$_{1-4}$alkyl, and —NHCOC$_{1-4}$alkyl.

It is also preferred that W is selected from one of the following NHCH$_2$CH=CH$_2$, NH$_2$, N(phthaloyl), NHCH$_3$, N(CH$_3$)$_2$, NO$_2$ and NHCO$_2$CH$_2$C$_6$H$_4$-p-NO$_2$.

In another aspect, the present invention provides compounds obtained by the processes defined above, preferably such compounds are selected from the following:

N-Allyl-1-(chloromethyl)-3-[(5,6,7-trimethoxy-1H-indol-2-yl)carbonyl]-1,2-dihydro-1H-benzo[e]indol-5-amine;
N-Allyl-1-(chloromethyl)-3-[(2E)-3-(4-methoxyphenyl)-2-propenoyl]-1,2-dihydro-1H-benzo[e]indol-5-amine;
1-(Chloromethyl)-3-[(5,6,7-trimethoxy-1H-indol-2-yl)carbonyl]-1,2-dihydro-1H-benzo[e]indol-5-amine:
1-(Chloromethyl)-3-[(2E)-3-(4-methoxyphenyl)-2-propenoyl]-1,2-dihydro-1H-benzo[e]indol-5-amine;
1-(Chloromethyl)-5-phthalimido-3-[(5,6,7-trimethoxyindol-2-yl)carbonyl]1,2-dihydro-3H-benz[e]indole
1-Chloromethyl-5-nitro-3-[5,6,7-trimethoxyindol-2-yl)-carbonyl]-1,2-dihydro-3H-benz[e]indole;
1-(Chloromethyl)-3-[[7-[2-(dimethylamino)ethoxy]-5-methoxyindol-2-yl]carbonyl]-5-nitro-1,2-dihydro-3H-benz[e]indole;
1-(Chloromethyl)-3-[[6-[2-(dimethylamino)ethoxy]-5-methoxyindol-2-yl]carbonyl]-5-nitro-1,2-dihydro-3H-benz[e]indole;
1-(Chloromethyl)-3-[(E)-3-methoxycinnamoyl]-5-nitro-1,2-dihydro-3H-benz[e]indole;
(R)-1-3-[(5,6,7-trimethoxyindol-2-yl)carbonyl]-1,2-dihydro-3H-benz[e]indole;
(S)-1-(Chloromethyl)-5-nitro-3-[(5,6,7-trimethoxyindol-2-yl)carbonyl]-1,2-dihydro-3H-benz[e]indole;
Methyl 1-(chloromethyl)-5-nitro-3-[(5,6,7-trimethoxyindol-2-yl)carbonyl]-1,2-dihydro-3H-pyrrolo[3,2-e]indole-7-carboxylate;
5-Amino-1-(chloromethyl)-3-[(5,6,7-trimethoxyindol-2-yl)carbonyl]-1,2-dihydro-3H-benz[e]indole;
1-(Chloromethyl)-5-methylamino-3-[(5,6,7-trimethoxyindol-2-yl)carbonyl]-1,2-dihydro-3H-benz[e]indole;
5-Amino-1-(chloromethyl)-3-[[7-[2-dimethylamino)ethoxy]-5-methoxyindol-2-yl]carbonyl]-1,2-dihydro-3H-benz[e]indole;
5-Amino-1-(chloromethyl)-3-[[6-[2-dimethylamino)ethoxy]-5-methoxyindol-2-yl]carbonyl]-1,2-dihydro-3H-benz[e]indole;
5-Amino-1-(chloromethyl)-3-[[7-[2-dimethylamino)ethoxy]-5-methoxyindol-2-yl]carbonyl]-1,2-dihydro-3H-benz[e]indole;
5-Amino-1-[(E)-4-butyrylamino-1-methyl-2-pyrroleacryloyl]-1-(chloromethyl)-1,2-dihydro-3H-benz[e]indole;
5-Amino-1-(chloromethyl)-3-[(E)-3-methoxycinnamoyl]-1,2-dihydro-3H-benz[e]indole;
(R)-5-Amino-1-(chloromethyl)-3-[(5,6,7-trimethoxyindol-2-yl)carbonyl]-1,2-dihydro-3H-benz[e]indole;
(S)-5-Amino-1-(chloromethyl)-3-[(5,6,7-trimethoxyindol-2-yl)carbonyl]-1,2-dihydro-3H-benz[e]indole;
Methyl 5-amino-1-(chloromethyl)-3-[(5,6,7-trimethoxyindol-2-yl)carbonyl]-1,2-dihydro-3H-pyrrolo[3,2-e]indole-7-carboxylate;
Methyl 1-(chloromethyl)-5-methylamino-3-[(5,6,7-trimethoxyindol-2-yl)carbonyl]-1,2-dihydro-3H-pyrrolo[3,2-e]indole-7-carboxylate;
Methyl 1-(chloromethyl)-5-dimethylamino-3-[(5,6,7-trimethoxyindol-2-yl)carbonyl]-1,2-dihydro-3H-pyrrolo[3,2-e]indole-7-carboxylate;
Methyl 1-(chloromethyl)-5-[(4-nitrobenzyloxycarbonyl)amino]-3-[(5,6,7-trimethoxyindol-2-yl)carbonyl]-1,2-dihydro-3H-pyrrolo[3,2-e]indole-7-carboxylate; and
1-(Chloromethyl)-5-[(4-nitrobenzyloxycarbonyl)amino]-3-[(5,6,7-trimethoxyindol-2-yl)carbonyl]-1,2-dihydro-3H-benz[e]indole;
or a physiologically functional derivative thereof.

In another aspect, the present invention relates to the use of the compounds obtained from one of the processes defined above as anticancer drugs. The compounds so obtained are used for the selective killing of oxic and hypoxic tumor cells in methods of treatment of cancers, for example leukemias and particularly solid cancers including breast, bowel and lung tumors, including small cell lung carcinoma.

In a further aspect, the present invention further relates to the use of some of the compounds obtained by the processes defined above that are suitable as substrates for nitroreductase or carboxypeptidase enzymes (for example, the aerobic NR2 nitroreductase isolated from *E. coli*) in methods of ADEPT and GDEPT therapy.

It is recognised that certain compounds produced by the methods of the present invention may exist in one of two different enantiomeric or diastereomeric forms. In such cases it is to be understood that the compounds prepared by the processes of the invention may represent either enantiomeric or diastereomeric form or a mixture of both.

A halogen group or -Hal depiction used throughout the specification is to be taken as meaning a fluoro, chloro, bromo or iodo group.

Physiologically functional derivatives of the compounds that are obtained by the processes defined above are to be understood as including salts, amides and esters. Esters include carboxylic acid esters in which the non-carbonyl moiety of the ester grouping is selected from straight or branched chain $C_{1-6}$ alkyl, (methyl, n-propyl, n-butyl or t-butyl); or $C_{3-6}$ cyclic alkyl (e.g. cyclohexyl). Salts include physiologically acceptable base salts, e.g. derived from an appropriate base, such as alkali metal (e.g. sodium), alkaline earth metal (e.g. magnesium) salts, ammonium and $NR^{4'''}$ (wherein $R^{4'''}$ is $C_{1-4}$ alkyl) salts. Other salts include acid addition salts, including the hydrochloride and acetate salts. Amides include non-substituted and mono- and di-substituted derivatives. Such derivatives are prepared by techniques known per se in the art of pharmacy.

Further aspects of the present invention will become apparent from the following description given by way of example only and with reference to the accompanying synthetic schemes.

DETAILED DESCRIPTION OF THE INVENTION

With reference to the following Scheme 1 a synthetic route to the compounds of Formula I is outlined as defined in the first aspect of the invention above.

In Scheme 1, conversion of 2,4-dinitro-1-hydroxynaphthalene (Martius Yellow; 1) to the iodide (3) is carried out by conversion to the trifluorosulfonate 2, followed by reaction with NaI. Concomitant reduction of the two nitro groups and removal of the iodine from 3 with $SnCl_2$ then gave the 1,3-diaminonaphthalene 4. Protection of the amines with BOC anhydride, followed by electrophilic iodination with NIS (general method of Boger et al., *J. Org. Chem.*, 2001 66, 5163), gave iodide 5. Allylation of the carbamate (NaH/allyl bromide) to give 6, followed by a $Bu_3SaH$ promoted 5-exo-trig free-radical cyclization of this with in situ TEMPO (general method of Boger et al.; *J. Org. Chem.*, 2001, 66, 5163) gave 7, which was subsequently reduced (Zn/AcOH) to the alcohol 8 in quantitative yield. The alcohol was converted to the chloride 9 with $Ph_3P/CCl_4$. Acid-catalyzed deprotection (TFA) of 9 followed by regioselective coupling with 4-methoxysuccinic acid using EDCI gave the required 10a. This was deblocked by a suitable reagent, (for example, Grubb's carbene [Alcaide et al., *Org. Lett.*, 2001, 3623] or preferably, sodium phenylsulfonate/camphorsulfonic acid/$Pd(Ph_3P)_4$ (modification of the method of Honda et al., J. Org. Chem. 1997, 62 8932) to the required 11a. This provides a 10-step synthesis of 11a from 1, with an overall yield of 32%. A similar synthesis gave the analogue 11b in 19% overall yield.

Scheme 1

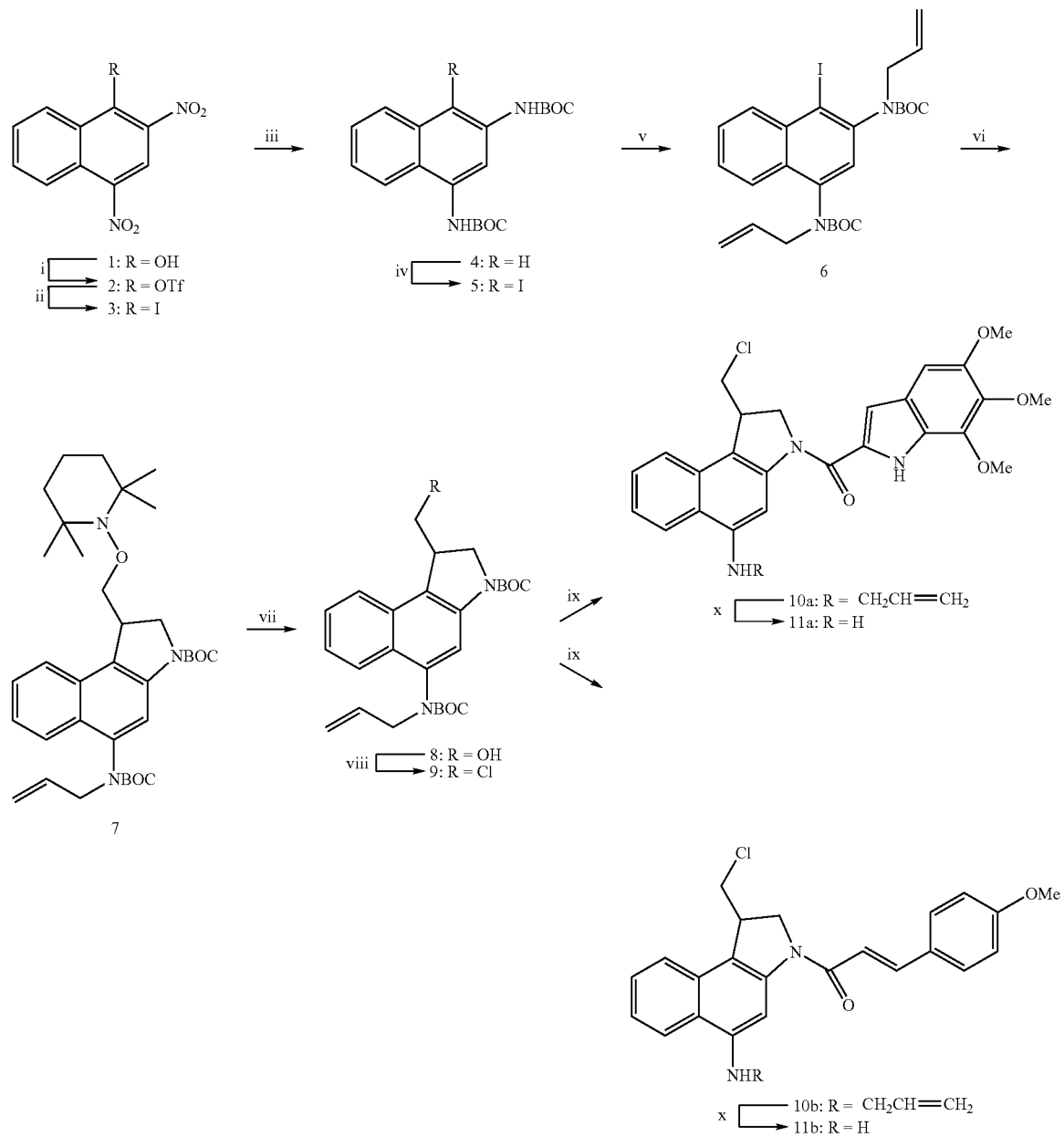

(i) TFSA/Et₃N;
(ii) NaI;
(iii) SnCl₂, then BOC₂O;
(iv) NIS then TsOH;
(v) NaH, then CH₂=CHCH₂Cl;
(vi) TEMPO/Bu₃SnH;
(vii) Zn powder;
(viii) Ph₃P then CCl₄;
(ix) TFA, then appropriate acid/EDCl;
(x) Grubb's carbene.

EXAMPLE 1

Synthesis of 10a and 10b by the Process of Scheme 1

A solution of Martius Yellow (1) (5.0 g, 21.4 mmol) in CH₂Cl₂ (100 mL) was treated with Et₃N (8 mL, 57 mmol), and the resulting solution was cooled with ice-salt bath and treated dropwise with trifluoromethanesulfonic anhydride (5 mL, 28 mmol). After stirring at room temperature for 2 h, 0.5 N HCl (100 mL) was added in one portion and the mixture was stirred for a further 30 min. The aqueous phase was separated and extracted with CH₂Cl₂ (2×50 mL). The combined organic phase was washed with sat. aq. NaHCO₃, brine, and was dried and concentrated under reduced pressure. The residue was purified by column chromatography on silica gel. Elution with CH₂Cl₂, gave 2,4-dinitro-1-naphthyl trifluoromethanesulfonate (2) (7.0 g, 89%) as yellow needles: mp (EtOAc/CH₂Cl₂) 105–107° C.; ¹H NMR [(CD₃)₂SO] δ 8.90 (s, 1H), 8.59 (m, 1H), 8.55 (m, 1H), 7.98

(m, 1H), 7.78 (m, 1H); $^{13}$C NMR δ 158.24, 135.07, 133.15, 127.92, 127.85, 127.73, 127.26, 125.54, 123.32, 122.42. Anal. ($C_{11}H_5F_3N_2O_7S$)C, H, N.

A solution of (2) (5.0 g, 13.7 mmol) and NaI (7.0 g) in EtOAc (200 mL) was heated under reflux for 2 h. The mixture was cooled to room temperature and washed with sat. aq. $Na_2S_2O_3$. The organic phase was dried, concentrated under reduced pressure, and the residue was purified by column chromatography on silica gel. Elution with $CH_2Cl_2$, gave 1-iodo-2,4-dinitronaphthalene (3) (4.3 g 91%) as yellow needle: mp (EtOAc/$CH_2Cl_2$) 194–195° C.; $^1$H NMR [($CD_3$)$_2$SO] δ 8.76 (s, 1H, H-3), 8.54 (m, 1H), 8.33 (m, 1H), 8.00(m, 2H); $^{13}$C NMR δ 151.81, 147.05, 134.97, 132.18, 131.24, 123.88, 123.26, 117.50, 102.66. Anal. ($C_{10}H_5IN_2O_4$) C, H, N.

A suspension of (3) (1.0 g, 2.9 mmol) and $SnCl_2.2H_2O$ (9.8 g, 436 mmol) in EtOAc (100 mL) was heated at reflux for 30 min. The white suspension was poured onto ice (ca. 100 g), and sat. aq. $NaHCO_3$ was added until the aqueous layer was basic as shown by litmus paper inspection. The mixture was extracted with ethyl acetate, the organic layer was washed with water, dried and the solvent was removed under reduced pressure to give crude 1,3-naphthalenediamine. This material was dissolved in THF (30 mL) and treated with $BOC_2O$ (3.0 g). The mixture was heated under reflux for 5 hrs. The solvent was removed and the residue was purified by column chromatography on silica gel. Elution with $CH_2Cl_2$ gave naphthalene-1,3-(bis-tertbutoxycarbamate) (4) (0.916 g, 88%) as a brown solid: mp (petroleum ether) 129–131° C.; $^1$H NMR (CDCl$_3$) δ 7.94 (s, 1H), 7.78 (s, 1H), 7.74 (m, 2H), 7.41 (m, 2H), 6.94 (s, 1H), 6.69 (s, 1H), 1.55 (s, 9H), 1.54 (s, 9H); $^{13}$C NMR δ 153.11, 152.75, 135.75, 134.75, 133.69, 128.47, 126.46, 124.36, 122.28, 119.67, 110.57, 110.47, 80.88, 80.57, 28.33. Anal ($C_{20}H_{26}N_2O_4$) C, H, N.

A solution of 4 (8.63 g, 24.1 mmol) in THF-$CH_3OH$ (200 mL, 1:1) at −78° C. was treated with N-iodosuccinimide (NIS, 8.5 g, 33.7-mmol) in THF (10 mL) followed by TsOH.$H_2O$ (9.5 g, 50.2 mmol) in $CH_3OH$ (10 mL). The reaction mixture was allowed to slowly warm to room temperature over 4 h and then diluted with 5% aqueous $Na_2S_2O_3$ and stirred at room temperature for 15 min. The reaction mixture was extracted with EtOAc (3×100 mL) and the combined extracts were dried and concentrated under reduced pressure. The residue was purified by column chromatography on silica gel. Elution with $CH_2Cl_2$ and crystallization from EtOAc/petroleum ether afforded 1-iodonaphthalene-2,4-(bis-tertbutoxycarbamate) (5) (9.46 g, 81%) as a brown solid: mp 154–156° C. (dec); $^1$H NMR (CDCl$_3$) δ 8.65 (s, 1H), 8.12 (m, 1H), 7.76 (m. 1H), 7.52 (m, 1H), 7.45 (m, 1H), 7.19 (s, 1H), 6.83 (s, 1H), 1.57 (s, 9H), 1.55 (s, 9H); $^{13}$C NR δ 153.14, 152.63, 138.20, 134.80, 134.59, 132.58, 128.16, 125.31, 124.78, 121.33, 113.52, 81.27, 81.04, 28.34. Anal. ($C_{10}H_5IN_2O_4$) C, H, N.

A solution of 5 (4.86 g, 10.0 mmol) in anhydrous DMF (150 mL) under nitrogen was treated with NaH (1.2 g, 30 mmol, 60% oil dispersion), and the reaction mixture was stirred for 30 min at 0° C. Allyl bromide (12.1 g, 100 mmol) was added dropwise over 5 min. and the solution was allowed to warm to room temperature and stirred for 2 h. Saturated aqueous $NaHCO_3$ (100 mL) was added, and the aqueous phase was extracted with EtOAc (3×100 mL). The combined extracts were dried, concentrated under reduced pressure, and the residue was purified by column chromatography on silica gel. Elution with EtOAc/petroleum ether (from 1:10 to 1:5), crystallization from EtOAc/petroleum ether afforded 1-iodonaphthalene-2,4-(bis-tert-butyl allyl-carbamate) (6) (5.64 g, 100%) as a white solid: mp 150–152° C.; $^1$H NMR (CDCl$_3$) δ 8.23 (m, 1H), 7.77 (m, 1H), 7.58 (m, 2H), 7.10 (m, 1H), 5.93 (m, 2H), 5.07 (m, 4H), 4.62 (m, 2H), 3.87 (m, 2H), 1.33 (s, 9H), 1.25 (s, 9H); $^{13}$C NMR δ 154.66, 153.74, 133.59, 133.45, 131.63, 128.06, 127.33, 127.25, 123.39, 123.32, 120.53, 118.26, 80.39, 52.76, 28.11. Anal. ($C_{26}H_{33}IN_2O_4$) C, H, N.

A solution of (6) (2.82 g, 5.0 mmol) in benzene (200 mL) was treated sequentially with TEMPO (2.34 g, 3.0 equiv) and $Bu_3SnH$ (1.0 equiv). The reaction mixture was warmed to 60° C. After 30 min, an additional 1 equiv of BuSnH was added. After 30 min, additional TEMPO (2 equiv) and $Bu_3SnH$ (1.0 equiv) were added. After 30 min, 2 equiv of TEMPO and 1 equiv of $Bu_3SnH$ in two separate portions at 20 min intervals were added. After 45 min at 60° C., the solvent was removed by evaporation, and the residue was purified by column chromatography on silica gel. Elution with EtOAc/petroleum ether (from 1:20 to 1:5), afforded N-allyl-(1-{[2,2,6,6-tetramethyl-1-piperidinyl)oxy]methyl}-1,2-dihydro-3H-benzo[e]indole-3,5-bis(carbamate) (7) (2.97 g, 100%) as a yellow gum: $^1$H (CDCl$_3$) δ 7.76 (m, 2H), 7.43 (m, 1H). 7.32 (m, 1H), 7.06 (s, 1H), 5.95 (m, 1H), 5.07 (m, 2H), 4.23 (m, 2H), 4.09 (m, 2H), 3.86 (m, 2H), 1.59 (s, 18H), 1.45–1.0 (m, 19H); $^{13}$C NMR δ 152.46, 134.04, 133.81, 129.89, 128.90, 126.35, 126.02, 123.82, 123.35, 117.51, 79.98, 59.87, 52.43, 39.66, 33.11, 28.51, 28.17, 20.11, 17.05.

A solution of (7) (2.97 g, 5.0 mmol) in THF-HOAc-$H_2O$ (3:1:1, 200 mL) was treated with Zn powder (30 g, 30 equiv), and the mixture was warmed at 70° C. for 10 h. The Zn powder was removed by filtration through Celite, and the mixture was concentrated under reduced pressure The residue was extracted with $CH_2Cl_2$ (3×100 mL) and the combined extracts were dried, concentrated under reduced pressure, and the crude product was purified by column chromatography on silica gel. Elution with EtOAc/petroleum ether (from 1:4 to 1:1), and crystallization from EtOAc/petroleum ether afforded N-allyl-(1-hydroxymethyl-1,2-dihydro-3H-benzo[e]indole-3,5-bis(carbamate) (8) (2.13 g, 94%) as a white solid: mp 125–128° C.; $^1$H NMR (CDCl$_3$) δ 7.75 (m, 2H), 7.43 (m, 1H), 7.34 (m, 1H), 7.06 (s, 1H), 5.98 (m, 1H), 5.11 (m, 2H), 4.20 (m, 2H), 4.11 (m, 2H), 3.90 (m, 2H), 1.59 (s, 18H), 1.26 (m, 1H); $^{13}$C NMR δ 152.92 159.99 152.46, 133.94, 128.89, 126.79, 126.00, 124.37, 123.91, 117.59, 64.69, 60.38, 52.11, 28.49, 28.15, 21.03. Anal. ($C_{10}H_5IN_2O_4$) C, H, N.

A solution of (8) (4.55 g, 10.0 mmol) in $CH_2Cl_2$ (100 mL) under nitrogen was treated sequentially with $Ph_3P$ (7.9 g, 30.0 mmol, 3 equiv) and $CCl_4$ (14.0 g, 90 mmol, 9 equiv). The reaction mixture was stirred at room temperature for 2 h. The solvent was evaporated under reduced pressure, and the crude product was purified by column chromatography on silica gel. Elution with EtOAc/petroleum ether (from 1:4 to 1:1), and crystallization from EtOAc/petroleum ether afforded N-allyl-(1-chloromethyl-1,2-dihydro-3H-benzo[e]indole)-3,5-bis(carbamate) (9) (4.46 g, 90%) as a yellow oil:
$^1$H NMR (CDCl$_3$) δ 7.78 (m, 1H), 7.70 (m, 1H), 7.50 (m, 2H), 7.38 (m, 1H), 5.98 (m, 1H), 5.10 (m, 2H), 4.20–3.40 (m, 6H), 1.60 (s, 18H), 1.20 (m, 1H); $^{13}$C NMR δ 154.90, 152.36, 133.88, 132.04, 128.43, 127.17, 124.42, 123.86, 122.46, 117.66, 60.38, 52.73,46.30, 28.47, 28.15, 21.03. HRMS m/z required for $C_{26}H_{33}ClN_2O_4$: 472.2129. Found: 472.2129.

A solution of 9 (406 mg, 0.858 mmol) in 50 mL of trifluoroacetic acid (TFA) was stirred under nitrogen at 0° C. for 2 h. The reaction mixture was then concentrated under reduced pressure, benzene (30 mL) was added and the mixture was concentrated once more. The resulting residue was treated with sat. aq. NaHCO$_3$, extracted with CH$_2$Cl$_2$ (3×50 mL) and the combined extracts were dried and concentrated under reduced pressure. To the resulting residue was added 5,6,7-trimethoxyindole-2-carboxylic acid (220 mg) and EDCI.HCl (411 mg), followed by DMA (10 mL). The reaction mixture was stirred at room temperature overnight and was diluted with sat. aq. NaHCO$_3$. The resulting mixture was extracted with EtOAc (3×50 mL) and the combined extracts were dried and concentrated under reduced pressure. The product was purified by column chromatography on silica gel. Elution with EtOAc/CH$_2$Cl$_2$ (1:5), and crystallization from CH$_2$Cl$_2$/diisopropyl ether afforded N-allyl-1-(chloromethyl)-3-[(5,6,7-trimethoxy-1H-indol-2-yl)carbonyl]-1,2-dihydro-3H-benzo[e]indol-5-amine (10a) (355 mg, 80%) as a yellow solid: mp 107–112° C.;

$^1$H NMR(CDCl$_3$) δ 9.45 (s, 1H), 7.82 (d, J=8.7 Hz, 1H), 7.81 (s, 1H), 7.70 (d, J=8.3 Hz, 1H), 7.51 (m, 1H), 7.37 (m, 1H), 7.00 (d, J=2.3 Hz, 1H), 6.88 (s, 1H), 6.05 (m, 1H), 5.40 (m, 1H), 5.26 (m, 1H), 4.76 (m, 2H), 4.61 (m, 1H), 4.07 (s, 3H), 4.02 (m, 3H), 3.95 (s, 3H), 3.91 (s, 3H), 3.42 (m, 1H), 1.64 (br, 1H) J=2.7 Hz; $^{13}$C NMR δ 160.40, 150.13, 144.91, 42.71, 140.41, 138.87, 134.49, 130.12, 130.04, 127.11, 125,48, 123.64, 123.41, 123.14, 121.25, 121.18, 116.99, 113.18, 106.39, 97.72, 96.88, 61.46, 61.09, 56.28, 55.14, 46.72, 46.14, 43.28. Anal. (C$_{10}$H$_5$IN$_2$O$_4$) C, H, N.

Benzenesulfinic acid, sodium salt (25 mg, 0.15 mmol) and camphorsulfonic acid (40 mg, 0.17 mmol) were added to a solution of 10a (30 mg, 0.059 mmol) in dichloromethane (5 mL). Pd(Ph$_3$P)$_4$ (5 mg, 0.004 mmol) was added and the reaction mixture was stirred at an ambient temperature for 30 min. The mixture was purified directly via a silica gel column. Elution with EtOAc/petroleum ether (1:1) gave 1-(chloromethyl)-3-[(5,6,7-trimethoxy-1H-indol-2-yl)carbonyl]-1,2-dihydro-3H-benzo[e]indol-5-amine (11a) (22 mg, 80%), spectroscopically identical to an authentic sample (Atwell et al., *J. Org Chem.*, 1998, 63, 9414).

Alternatively, a solution of 10a (70 mg, 0.138 mmol) in anhydrous toluene (5 mL) (under N$_2$ and protected from light), was heated at reflux and treated every 20 min with small portions of Cl$_2$(Cy$_3$P)$_2$Ru=CHPh (Alcaide et al., *Org. Lett.*, 2001, 3623) (overall total 0.02 mmol). After 8 h, the resulting mixture was concentrated under reduced pressure. Chromatography of the residue eluting with EtOAc/CH$_2$Cl$_2$ gave 17 mg of recovered starting material and 11a (27 mg, 55% based on consumption of starting material). The product was crystallized from CH$_2$Cl$_2$/diisopropyl ether and was spectroscopically identical to an authentic sample (Atwell et al., *J. Org. Chem.*, 1998, 63, 9414).

Similarly, 9 (2.74 g, 5.81 mmol) was treated with TFA (50 mL) 2 h and worked up as above. The crude product was stirred at an ambient temperature overnight with 4-methoxycinnamic acid (1.14 g, 6.4 mmol) and EDCI.HCl (2.77 g) in DMA (10 mL). Workup, and column chromatography of the product on silica gel, eluting with EtOAc/CH$_2$Cl$_2$ (1:5), followed by crystallization from CH$_2$Cl$_2$/diisopropyl ether, gave N-allyl-1-(chloromethyl)-3-[(2E)-3-(4-methoxyphenyl)-2-propenoyl]-1,2-dihydro-1H-benzo[e]indol-5-amine (10b) (980 mg, 39%) as a yellow solid: mp 152–154° C.; $^1$H NMR (CDCl$_3$) δ 7.95 (br, 1H), 7.80 (s, 1H), 7.79 (d, J=8.5 Hz, 1H), 7.68 (d, J=8.2 Hz, 1H), 7, 57 (s, 1H), 7.55 (s, 1H), 7.48 (m, 1H), 7.33 (m, 1H), 6.93 (m, 1H), 6.91 (s, 1H), 6.80 (br, 1H), 6.09 (m, 1H), 5.40 (m, 1H), 5.26 (m, 1H), 4.49 (m, 1H), 4.36 (m, 1H), 4.00 (m, 5H), 3.85 (s, 3H), 3.41 (m, 1H); $^{13}$C NMR δ 164.95, 161.23, 144.95, 143.49, 142.64, 134.56, 130.11, 129,77, 127.77, 127.02, 123,16, 123.02, 121.15, 121.00, 116.99, 116,30, 114.32, 96.91, 55.38, 53.39, 46.73, 46.33, 42.55.

A solution of 10b (691 mg, 1.6 mmol) in dichloromethane (20 mL) was treated with benzenesulfinic acid, sodium salt (524 mg, 3.2 mmol), camphorsulfonic acid (742 mg, 3.2 mmol) and Pd(Ph$_3$P)$_4$ (92 mg, 0.08 mmol) as described above. The mixture was stirred under an inert atmosphere at an ambient temperature until all starting material was consumed (typically 15 min. however the reaction is dependent on the quality of the Pd(Ph$_3$P)$_4$ used and it is sometimes necessary to add an extra portion of the catalyst). The mixture was directly aspirated onto a 4 mm Chromatotron radial chromatography plate and the product was eluted as the major yellow band with 25% EtOAc/hexanes. The combined fractions were concentrated under reduced pressure to give 1-(chloromethyl)-3-[(2E)-3-(4-methoxyphenyl)-2-propenoyl]-1,2-dihydro-3H-benzo[e]indol-5-amine (11b) (547 mg, 87%), identical with an authentic sample (Atwell et al., *J. Org. Chem.* 1998, 63, 9414).

Alternatively, deprotection of 10b (90 mg) with Cl$_2$(Cy$_3$P)$_2$Ru=CHPh as described above followed by chromatography of the residue, eluting with EtOAc/CH$_2$Cl$_2$, gave 11b (34 mg, 42%). Crystallization from CH$_2$Cl$_2$/diisopropyl ether gave a product spectroscopically identical to an authentic sample.

The amino compounds of formula I can also be oxidised to the corresponding nitro compounds (such as those described in U.S. Pat. No. 6,130,237) by a variety of methods, including peracetic acid (Sakaue et al, *J. Org. Chem.*, 1993, 58, 3633) or zirconium alkoxides (Krohn, *Synthesis*, 1997, 10, 1115; Krohn et al., *J. Prakt. Chem.* 1997, 339, 335). Thus oxidation of 11a with sodium perborate/acetic acid in THF gives the corresponding nitro compound.

It will be apparent to those skilled in the art that the processes of the present invention could be readily applied without undue experimentation and with appropriate selection of starting material so that other examples of Formula (I) could be expeditiously prepared. For example, many of the carbamate protecting groups envisaged that could be prepared for the amine of group W are described in WO00/64864. The disclosure of WO00/64864 is incorporated herein in its entirety. Similarly, it is to be appreciated that all tie compounds described in U.S. Pat. No. 6,130,237 could be prepared by the methods of the present invention. The disclosure of U.S. Pat. No. 6,130,237 is also incorporated herein in its entirety.

It is an advantage of the processes of the present invention that the processes described above of Schemes 1 and 2 provide significantly higher-yielding synthetic routes to the general class of 3-substituted 1-(chloromethyl)-1,2-dihydro-1H-benzo[e]indol-5-ylamines.

GDEPT (gene-directed enzyme prodrug therapy for cancer) is a tool suitable for use with some of the compounds that are capable of being produced by the processes of the present invention. The following GDEPT systems that are relevant to the compounds produced by the processes of the present invention include:

(i) Vector Systems

In general, the vector for use in GDEPT therapies can be any suitable DNA or RNA vector.

Suitable viral vectors include those that are based upon a retrovirus. Such vectors are widely available in the art. Huber et al. (ibid) report the use of amphotropic retroviruses for the transformation of hepatoma, breast, colon or skin cells. Culver et al. (*Science* (1992) 256; 1550–1552) also describe the use of retroviral vectors in GDEPT. Such vectors or vectors derived from them may also be used. Other retroviruses may also be used to make vectors suitable for use in the present invention. Such retroviruses include rous sarcoma virus (RSV).

Englehardt et al. (*Nature Genetics* (1993) 4; 27–34) describe the use of adenovirus-based vectors in the delivery of the cystic fibrosis transmembrane conductance product (CFTR) into cells, and such adenovirus-based vectors may also be used.

Vectors utilising adenovirus promoter and other control sequences are of use in delivering a system according to the invention to cells in the lung, and hence useful in treating lung tumours.

Other vector systems including vectors based on the Molony murine leukaemia virus are known (Ram, Z. et al., *Cancer Research* (1993) 53; 83–88; Dalton & Treisman, Cell (1992) 68; 597–612). These vectors contain the Murine Leukaemia virus (MLV) enhancer cloned upstream at a .beta-globin minimal promoter. The beta-globin 5' untranslated region up to the initiation ATG is supplied to direct efficient translation of the enzyme.

Suitable promoters which can be used in vectors described above, include MLV, CMV, RSV and adenovirus promoters. Preferred adenovirus promoters are the adenovirus early gene promoters. Strong mammalian promoters may also be suitable. An example of such a promoter is the EF-1.alpha. promoter which may be obtained by reference to Mizushima and Nagata ((1990), *Nucl. Acids Res.* 18; 5322). Variants of such promoters retaining substantially similar transcriptional activities may also be used.

(ii) Nitroreductase

Compounds obtained by the present invention of the formula (I) which is a substrate suitable for a nitroreductase or carboxypeptidase enzyme in which P is group (IIa) or (IIb) or (IIe) and compounds of the formula (I) in which Y is a group $NO_2$ or N(O)RR can be activated by reduction of the group P or Y (as defined above) by nitroreductase.

Preferably, the enzyme is a non-mammalian nitroreductase enzyme, such as a bacterial nitroreductase. An *E. coli* nitroreductase as disclosed in WO93/08288 is particularly preferred. The enzyme may be modified by standard recombinant DNA techniques, e.g. by cloning the enzyme, determining its gene sequence and altering the gene sequence by methods such as truncation, substitution, deletion or insertion of sequences for example by site-directed mutagenesis. Reference may be made to "*Molecular Cloning*" by Sambrook er al (1989, Cold Spring Harbor) for discussion of standard recombinant DNA techniques. The modification made may be any which still leaves the enzyme with the ability to reduce the nitro group of the protecting group P in the compound of formula (I) or the nitro or amine N-oxide groups when these are represented by Y in formula (I) but alters other properties of the enzyme, for example its rate of reaction or selectivity.

In addition, small truncations in the N- and/or C-terminal sequence may occur as a result of the manipulations required to produce a vector in which a nucleic acid sequence encoding the enzyme is linked to the various other vector sequences.

(iii) Carboxypeptidase

Compounds obtained by the present invention of the formula (I) in which P is group (IIc) can be activated by removal of the group P by a carboxypeptidase. The enzyme is preferably a bacterial carboxypeptidase, especially carboxypeptidase CPG2 or *Pseudomonas* γ-glutamylhydrolase EC3.4.22.12 (Levy, C. C. & Goldman, P., *J. Biol. Chem.* 242; p 2933 (1967).

Carboxypeptidase G2 (CPG2) is disclosed in WO88/07378. Although native CPG2 is preferred, alterations to its sequence which are amino acid substitutions, deletions or insertions (e.g. of about 1, 2, 3, 4, 5, 10 or 20 residues in each case) are also possible. In any event, the alteration will be such that the enzyme retains its ability to convert a prodrug to an active drug at substantially the same rate as the native enzyme. In this context, "substantially the same rate" will desirably be within 1 order of magnitude, and preferably from about 50-fold e.g. about 2-fold less to 2, 5 or 10 fold more.

In addition to specific changes the enzyme may otherwise be altered by truncation, substitution, deletion or insertion as long as the activity of the enzyme is substantially unchanged as defined above. For example, small truncations in the N- and/or C-terminal sequence may occur as a result of the manipulations required to produce a vector in which a nucleic acid sequence encoding the enzyme is linked to a suitable promoter.

ADEPT (antibody-directed enzyme prodrug therapy for cancer) is a tool suitable for use with some of the compounds that are capable of being produced by the processes of the present invention.

For applications in ADEPT systems, an antibody directed against a tumour specific marker is linked to the nitroreductase or carboxypeptidase enzyme, which may be modified as described above. The antibody may be monoclonal or polyclonal. For the purposes of the present invention, the term "antibody", unless specified to the contrary, includes fragments of whole antibodies which retain their binding activity for a tumour target antigen. Such fragments include Fv, F(ab') and F(ab')2 fragments, as well as single chain antibodies. Furthermore, the antibodies and fragments thereof may be humanised antibodies, e.g. as described in EP-A-239400.

The antibodies may be produced by conventional hybridoma techniques or, in the case of modified antibodies or fragments, by recombinant DNA technology, e.g. by the expression in a suitable host vector of a DNA construct encoding the modified antibody or fragment operably linked to a promoter. Suitable host cells include bacterial (e.g. *E. coli*), yeast, insect and mammalian. When the antibody is produced by such recombinant techniques the enzyme may be produced by linking a nucleic acid sequence encoding the enzyme (optionally modified as described above) to the 3' or 5' end of the sequence of the construct encoding the antibody or fragment thereof.

Applications of the Compounds Obtained by the Processes of the Present Invention The compounds of formula (I) obtained from the processes of the present invention can be used in a method of treatment of the human or animal body. Such treatment includes a method of treating the growth of neoplastic cells in a patient with neoplastic disease which comprises administering to a patient in need of treatment compounds of formula (I) of the invention, or where the compounds of formula (I) obtained are suitable as substrates as part of an ADEPT or GDEPT therapy system. Neoplastic diseases include leukaemia and solid tumours such as breast, bowel and lung tumours including small cell lung carcinoma.

It will be understood that where treatment of tumours is concerned, treatment includes any measure taken by the physician to alleviate the effect of the tumour on a patient.

Thus, although complete remission of the tumour is a desirable goal, effective treatment will also include any measures capable of achieving partial remission of the tumour as well as a slowing down in the rate of growth of a tumour including metastases. Such measures can be effective in prolonging and/or enhancing the quality of life and relieving the symptoms of the disease.

(i) Compounds of the Formula (I) Obtained by a Process of the Present Invention

Compounds of the formula (1) obtained by the processes of the present invention can be used in a method of treatment of neoplastic disease in a patient, which method comprises administering to a patient in need of treatment an effective amount of a compound of formula (i). The compounds obtained may be administered in the form of a pharmaceutical composition.

While the exact dose of the compound will be at the discretion of the physician, taking account of the condition and needs of the patient, typical doses will be in the range of from about 0.1 to 200 mg/Kg, preferably about from 10 to 100 mg/Kg per patient per day.

(ii) ADEPT Therapy

The antibody/enzyme conjugate for ADEPT can be administered simultaneously but it is often found preferable, in clinical practice, to administer the enzyme/agent conjugate before the prodrug, e.g. up to 72 hours or even 1 week before, in order to give the enzyme/agent conjugate an opportunity to localise in the region of the tumour target. By operating in this way, when the prodrug is administered, conversion of the prodrug to the cytotoxic agent tends to be confined to the regions where the enzyme/agent conjugate is localised, i.e. the region of the target tumour the premature release of the toxic fragment of formula (I) is minimised.

In ADEPT the degree of localisation of the enzyme/agent conjugate (in terms of the ratio of localized to freely circulating active conjugate) can be further enhanced using the clearance and/or inactivation systems described in WO89/10140. This involves, usually following administration of the conjugate and before administration of the prodrug, the administration of a component (a "second component") which is able to bind to the part of the conjugate so as to inactivate the enzyme and/or accelerate the clearance of the conjugate from the blood. Such a component may include an antibody to the enzyme component of the system which is capable of inactivating the enzyme.

The second component may be linked to a macromolecule such as dextran, a liposome, albumin, macroglobulin or a blood group O erythrocyte so that the second component is restrained from leaving the vascular compartment. In addition or as an alternative, the second component may include a sufficient number of covalently bound galactose residues, or residues of other sugars such as lactose or mannose, so that it can bind the conjugate in plasma but be removed together with the conjugate from plasma by receptors for galactose or other sugars in the liver. The second component should be administered and designed for use such that it will not, to any appreciable extent, enter the extravascular space of the tumour where it could inactivate localised conjugate prior to and during administration of the prodrug.

In ADEPT systems, the dose of the prodrug and conjugate will ultimately be at the discretion of the physician, who will take into account such factors as the age, weight and condition of the patient. Suitable doses of prodrug and conjugate are given in Bagshawe et al. Antibody, Immunoconjugates, and Radiopharmaceuticals (1991), 4, 915–922.

A suitable dose of conjugate may be from 500 to 200,000 enzyme units/m$^2$ (e.g. 20,000 enzyme units/m$^2$) and a suitable dose of prodrug may be from about 0.1 to 200 mg/Kg, preferably about from 10 to 100 mg/Kg per patient per day.

In order to secure maximum concentration of the conjugate at the site of desired treatment, it is normally desirable to space apart administration of the two components by at least 4 hours. The exact regime will be influenced by various factors including the nature of the tumour to be targeted and the nature of the prodrug, but usually there will be an adequate concentration of the conjugate at the site of desired treatment within 48 hours.

The ADEPT system when used with nitroreductase also preferably comprises a suitable cofactor for the enzyme. Suitable cofactors include a riboside or riboside of nicotinic acid or nicotinamide.

The antibody/enzyme conjugate may be administered by any suitable route usually used in ADEPT therapy.

(iii) GDEPT Therapy

For use of the vectors in therapy, the vectors will usually be packaged into viral particles and the particles delivered to the site of the tumour, as described in for example Ram et al. (ibid). The viral particles may be modified to include an antibody, fragment thereof (including a single chain) or tumour-directed ligand to enhance targeting of the tumour. Alternatively the vectors may be packaged into liposomes. The liposomes may be targeted to a particular tumour. This can be achieved by attaching a tumour-directed antibody to the liposome. Viral particles may also be incorporated into liposomes. The particles may be delivered to the tumour by any suitable means at the disposal of the physician. Preferably, the viral particles will be capable of selectively infecting the tumour cells. By "selectively infecting" it is meant that the viral particles will primarily infect tumour cells and that the proportion of non-tumour cells infected is such that the damage to non-tumour cells by administration of a pro drug will be acceptably low, given the nature of the disease being treated. Ultimately, this will be determined by the physician.

One suitable route of administration is by injection of the particles in a sterile solution. Viruses, for example isolated from packaging cell lines may also be administered by regional perfusion or direct intratumoral direction, or direct injection into a body cavity (intracaviterial administration), for example by intraperitoneum injection.

The exact dosage regime for ADEPT will, of course, need to be determined by individual clinicians for individual patients and this, in turn, will be controlled by the exact nature of the prodrug and the cytotoxic agent to be released from the prodrug but some general guidance can be given. Chemotherapy of this type will normally involve parenteral administration of modified virus and administration by the intravenous route is frequently found to be the most practical.

In GDEPT systems the amount of virus or other vector delivered will be such as to provide a similar cellular concentration of enzyme as in the ADEPT system mentioned above. Typically, the vector will be administered to the patient and then the uptake of the vector by transfected or infected (in the case of viral vectors) cells monitored, for example by recovery and analysis of a biopsy sample of targeted tissue. This may be determined by clinical trials which involve administering a range of trial doses to a patient and measuring the degree of infection or transfection of a target cell or tumour. The amount of prodrug required will be similar to or greater than that for ADEPT systems.

In using a GDEPT system the prodrug will usually be administered following administration of the vector encoding an enzyme. Suitable doses of prodrug are from about 0.1 to 200 mg/Kg, preferably about from 10 to 100 mg/Kg per patient per day.

Wherein the foregoing description reference has been made to reagents, or integers having-known equivalents thereof, then: those-equivalents are herein incorporated as if individually set forth.

While this invention has been described with reference to certain embodiments and examples, it is to be appreciated that further modifications and variations may be made to embodiments and examples without departing from the spirit or scope of the invention.

The invention claimed is:

1. A process of preparing a compound of formula (I)

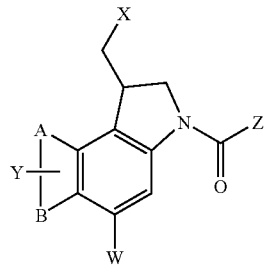
(I)

wherein

A and B together may represent a fused optionally substituted benzene and a fused optionally substituted naphthalene, where the optional substituents are represented by Y; wherein Y is selected from one or more of H, a halogen, $CH_3$, $OR^1$, $SR^1$, $NR^1R^2$, $SO_2R^1$, $CONHR^1$, CN or $CO_2R^1$ where $R^1$ or $R^2$ each independently represents H, lower $C_{1-4}$ alkyl or a benzene ring, optionally substituted with one or more hydroxyl, $NO_2$ or amino groups, the amino groups being further optionally substituted with one or two $C_1-C_4$ alkyl groups, X is halogen or $OSO_2R$, where R represents H, lower $C_{1-4}$ alkyl or a benzene ring, optionally substituted with one or more hydroxyl, $NO_2$ or amino groups, the amino groups being further optionally substituted with one or two $C_1-C_4$ alkyl groups, W is selected from $NO_2$, NHOH, $N(R^3)_2$ $NHR^3$, $NHCO_2R^3$, N(phthaloyl) or $NH_2$, where each $R^3$ is selected from a $C_{1-4}$ alkyl group optionally substituted with one or more hydroxyl or amino groups, each amino group being optionally substituted with one or two $C_{1-4}$ alkyl groups; a $C_{1-4}$ alkylene group optionally substituted with hydroxyl or amino groups, each amino group being optionally substituted with one or two $C_{1-4}$ alkyl groups; or a benzene ring, optionally substituted with one or more hydroxyl, $NO_2$ or amino groups, the amino groups being further optionally substituted with one or two $C_1-C_4$ alkyl groups, or W is further selected from the group

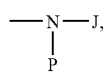

wherein J is selected from OH or R wherein R represents H, lower $C_{1-4}$ alkyl or a benzene ring, optionally substituted with one or more hydroxyl, $NO_2$ or amino groups, the amino groups being further optionally substituted with one or two $C_1-C_4$ alkyl groups, and P is a group which is a substrate suitable for a nitroreductase or carboxypeptidase enzyme such that one of said enzymes is able to bring about the removal of the group P which is selected from the following moieties:

—C(O)—(CZ'$_2$)$_n$—Ph (IIa)

—C(O)—O—CH$_2$—Ph (IIb)

—C(O)—NH—C(COOH)—(CH$_2$)$_2$—COOH (IIc)

—C(O)—O—CH$_2$-Phe-L-C(O)—NH—C(COOH)—CH$_2$—COOH (IId)

—C(O)—O—CH$_2$—IMDZ (IIe)

—C(O)—O—CH$_2$-Furyl (IIf)

—C(O)—O—CH$_2$-Thienyl (IIg)

—C(O)—O—CH$_2$-Pyrrolyl (IIh)

wherein each occurrence of Z' is independently H or $CH_3$, n is 1 or 2, Ph is a phenyl moiety substituted in the moiety of (IIa) by a nitro group at the 2-position, and substituted in the moiety of (IIb) by a nitro group in the 2- or 4-position, IMDZ is an imidazolyl moiety substituted in the moiety of (IIe) by a nitro group in the 2-, 4- or 5-position, and optionally further substituted by —$CH_3$, or $C_1-C_4$ alkyl at the 1-position, wherein said alkyl is further substituted by OH, Phe is a phenylene ($C_6H_4$) ring in which the group -L, which may represent O or NH, is para to the group —$OCH_2$, wherein the Furyl, Thienyl, and Pyrrolyl groups in moieties, (IIf), (IIg) and (IIh) respectively are optionally substituted by a nitro group, wherein the Pyrrolyl group of (IIh) is further optionally substituted at the 1-position by $CH_3$ and/or $CO_2CH_2CH_3$ at the 2-position, the groups Ph and Phe, being further optionally substituted by a group $R^1$ which is a group selected from R, CONHR, NHCOR, NHR, OR or $SO_2R$ where R represents H, lower $C_{1-4}$ alkyl optionally substituted by morpholino, or a benzene ring, optionally substituted with one or more hydroxyl, $NO_2$ or amino groups, the amino groups being further optionally substituted with one or two $C_1-C_4$ alkyl groups; Z is selected from the following structures (Ia, Ib, Ic or Id)

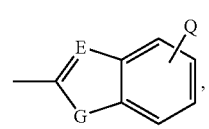
Ia

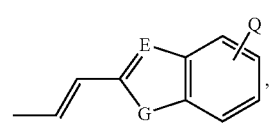
Ib

-continued

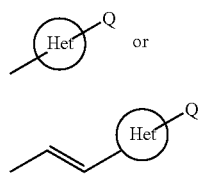

wherein E is selected from —N═, or —CH═,
G is O, S, or NH,
Q is either
(a) absent or independently selected from one to three of R, —OR, halogen, —NRR, —NO$_2$, —COOR, —CONRR, —NRCOR, OP(O)(OH)$_2$, O(CH$_2$)$_n$P(O)(OH)$_2$, (CH$_2$)$_n$OP(O)(OH)$_2$,

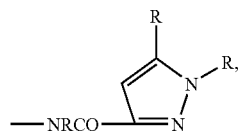

or a fused

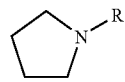

group;
where R represents H, lower C$_{1-4}$ alkyl or a benzene ring, optionally substituted with one or more hydroxyl or amino groups, each amino group being optionally substituted with one or two C$_1$–C$_4$ alkyl groups and where n represents 1, 2 or 3; or (b) is an additional group of formulae (Ia, Ib, Ic or Id); and
HET may represent a 5- or 6-membered carbocycle or heterocycle containing one or two atoms independently selected from N, O and S;
or a physiologically functional derivative thereof,
wherein the process for preparing a compound of formula I comprises the steps of
(a) converting the NO$_2$ groups of a compound of formula (I') into NHBOC groups of a compound of formula (II')

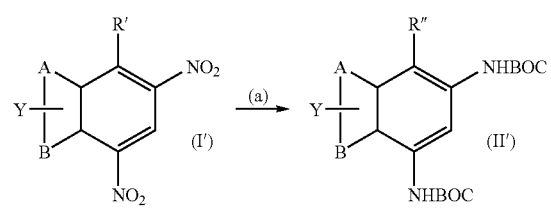

R' = OH
R' = OTf
R' = Halogen

R'' = H
R'' = Halogen wherein the variables A, B, and Y are as defined above in this claim,
(b) converting a compound of formula (II') by allylation of the NHBOC groups into a compound of formula (III')

wherein the variables A, B, and Y are as defined above in this claim,
(c) converting a compound of formula (III') into an indole derivative of formula (IV')

wherein the variables A, B, and Y are as defined above,
(d) reacting the compound of Formula (IV') in the presence of Zn powder to give a compound of Formula (V')

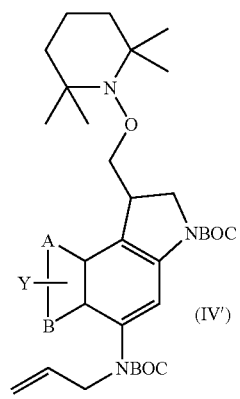

(d) →

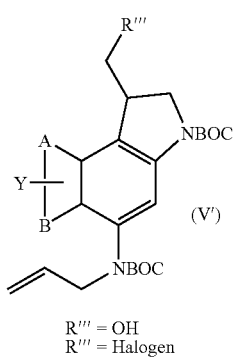

R''' = OH
R''' = Halogen wherein the variables A, B, and Y are as defined above in this claim, and (e) reacting the NBOC and allyl groups of Formula (V') as desired to give a compound of Formula (I)

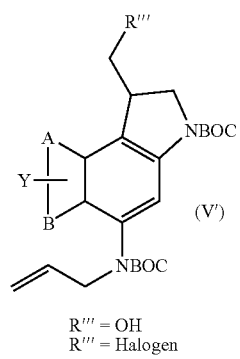

R''' = OH
R''' = Halogen (e) →

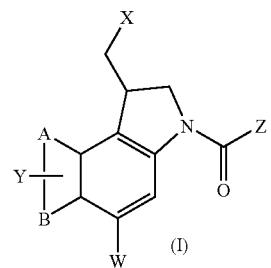

wherein the variables A, B, Y, W, and Z are as defined above.

2. The process according to claim 1 wherein A—B represents a fused benzo group.

3. The process according to claim 1 wherein X represents chloro.

4. The process according to claim 1 wherein Z represents one of following groups:

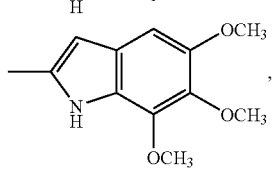

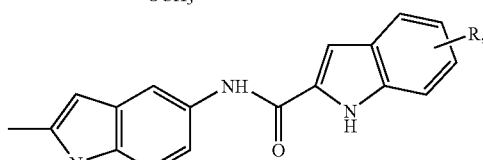

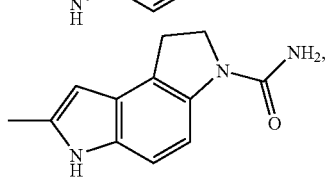

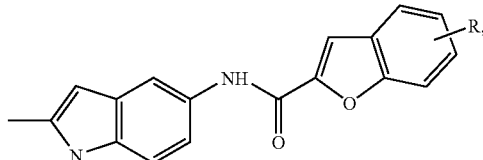

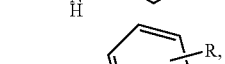

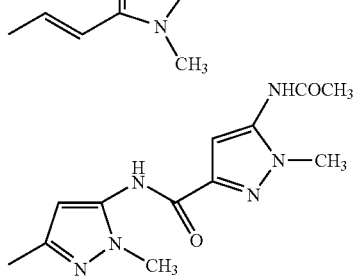

wherein the substituent —R may represent one or more substituents selected from —H, —OH, halogen, —NO$_2$, —NH$_2$, —N(C$_{1-4}$ alkyl)$_2$, —C$_{1-4}$ alkyl, —COOC$_{1-4}$ alkyl, —OC$_{1-4}$ alkyl, and —NHCOC$_{1-4}$ alkyl.

5. The process according to any one of claim 1 wherein W is selected from NHCH$_2$CH═CH$_2$, NH$_2$, N(phthaloyl), NHCH$_3$, N(CH$_3$)$_2$, NO$_2$, and NHCO$_2$CH$_2$C$_6$H$_4$-p-NO$_2$.

6. The process according to claim 1 wherein the compound of Formula 1 is selected from:

N-Allyl-1-(chloromethyl)-3-[(5,6,7-trimethoxy-1H-indol-2-yl)carbonyl]-1,2-dihydro-3H-benzo[e]indol-5-amine;
N-Allyl-1-(chloromethyl)-3-[(2E)-3-(4-methoxyphenyl)-2-propenoyl]-1,2-dihydro-3H-benzo[e]indol-5-amine;
1-(Chloromethyl)-3-[(5,6,7-trimethoxy-1H-indol-2-yl)carbonyl]-1,2-dihydro-3H-benzo[e]indol-5-amine;
1-(Chloromethyl)-3-[(2E)-3-(4-methoxyphenyl)-2-propenoyl]-1,2-dihydro-3H-benzo[e]indol-5-amine;
1-(Chloromethyl)-5-phthalimido-3-[(5,6,7-trimethoxyindol-2-yl)carbonyl]-1,2-dihydro-3H-benz[e]indole
1-Chloromethyl-5-nitro-3-[5,6,7-trimethoxyindol-2-yl)-carbonyl]-1,2-dihydro-3H-benz[e]indole;
1-(Chloromethyl)-3-[[7-[2-(dimethylamino)ethoxy]-5-methoxyindol-2-yl]carbonyl]-5-nitro-1,2-dihydro-3H-benz[e]indole;
1-(Chloromethyl)-3-[[6-[2-(dimethylamino)ethoxy]-5-methoxyindol-2-yl]carbonyl]-5-nitro-1,2-dihydro-3H-benz[e]indole;
1-(Chloromethyl)-3-[(E)-3-methoxycinnamoyl]-5-nitro-1,2-dihydro-3H-benz[e]indole;
(R)-1-(Chloromethyl)-5-nitro-3-[(5,6,7-trimethoxyindol-2-yl)carbonyl]-1,2-dihydro-3H-benz[e]indole;
(S)-1-(Chloromethyl)-5-nitro-3-[(5,6,7-trimethoxyindol-2-yl)carbonyl]-1,2-dihydro-3H-benz[e]indole;
Methyl 1-(chloromethyl)-5-nitro-3-[(5,6,7-trimethoxyindol-2-yl)carbonyl]-1,2-dihydro-3H-pyrrolo[3,2-e]indole-7-carboxylate;
5-Amino-1-(chloromethyl)-3-[(5,6,7-trimethoxyindol-2-yl)carbonyl]-1,2-dihydro-3H-benz[e]indole;
1-(Chloromethyl)-5-methylamino-3-[(5,6,7-trimethoxyindol-2-yl)carbonyl]-1,2-dihydro-3H-benz[e]indole;
5-Amino-1-(chloromethyl)-3-[[7-[2-dimethylamino)ethoxy]-5-methoxyindol-2-yl]carbonyl]-1,2-dihydro-3H-benz[e]indole;
5-Amino-1-(chloromethyl)-3-[[6-[2-dimethylamino)ethoxy]-5-methoxyindol-2-yl]carbonyl]-1,2-dihydro-3H-benz[e]indole;
5-Amino-1-(chloromethyl)-3-[[7-[2-dimethylamino)ethoxy]-5-methoxyindol-2-yl]carbonyl]-1,2-dihydro-3H-benz[e]indole;
5-Amino-1-[(E)-4-butyrylamino-1-methyl-2-pyrroleacryloyl]-1-(chloromethyl)-1,2-dihydro-3H-benz[e]indole;
5-Amino-1-(chloromethyl)-3-[(E)-3-methoxycinnamoyl]-1,2-dihydro-3H-benz[e]indole;
(R)-5-Amino-1-(chloromethyl)-3-[(5,6,7-trimethoxyindol-2-yl)carbonyl]-1,2-dihydro-3H-benz[e]indole;
(S)-5-Amino-1-(chloromethyl)-3-[(5,6,7-trimethoxyindol-2-yl)carbonyl]-1,2-dihydro-3H-benz[e]indole;
Methyl 5-amino-1-(chloromethyl)-3-[(5,6,7-trimethoxyindol-2-yl)carbonyl]-1,2-dihydro-3H-pyrrolo[3,2-e]indole-7-carboxylate;
Methyl 1-(chloromethyl)-5-methylamino-3-[(5,6,7-trimethoxyindol-2-yl)carbonyl]-1,2-dihydro-3H-pyrrolo[3,2-e]indole-7-carboxylate;
Methyl 1-(chloromethyl)-5-dimethylamino-3-[(5,6,7-trimethoxyindol-2-yl)carbonyl]-1,2-dihydro-3H-pyrrolo[3,2-e]indole-7-carboxylate;
Methyl 1-(chloromethyl)-5-[(4-nitrobenzyloxycarbonyl)amino]-3-[(5,6,7-trimethoxyindol-2-yl)carbonyl]-1,2-dihydro-3H-pyrrolo[3,2-e]indole-7-carboxylate; and
1-(Chloromethyl)-5-[(4-nitrobenzyloxycarbonyl)amino]-3-[(5,6,7-trimethoxyindol-2-yl)carbonyl]-1,2-dihydro-3H-benz[e]indole;

or a physiologically functional derivative thereof.

7. The process according to claim 6 wherein the compound of Formula 1 is selected from:
N-Allyl-1-(chloromethyl)-3-[(5,6,7-trimethoxy-1H-indol-2-yl)carbonyl]-1,2-dihydro-3H-benzo[e]indol-5-amine; N-Allyl-1-(chloromethyl)-3-[(2E)-3-(4-methoxyphenyl)-2-propenoyl]-1,2-dihydro-3H-benzo[e]indol-5-amine;
1-(Chloromethyl)-3-[(5,6,7-trimethoxy-1H-indol-2-yl)carbonyl]-1,2-dihydro-3H-benzo[e]indol-5-amine; and
1-(Chloromethyl)-3-[(2E)-3-(4-methoxyphenyl)-2-propenoyl]-1,2-dihydro-3H-benzo[e]indol-5-amine.

8. A compound obtained by the process according to claim 1 selected from: N-Allyl-1-(chloromethyl)-3-[(5,6,7-trimethoxy-1H-indol-2-yl)carbonyl]-1,2-dihydro-3H-benzo[e]indol-5-amine; N-Allyl-1-(chloromethyl)-3-[(2E)-3-(4-methoxyphenyl)-2-propenoyl]-1,2-dihydro-3H-benzo[e]indol-5-amine; and 1-(chloromethyl)-5-phthalimido-3-[5,6,7-trimethoxyindol-2-yl)carbonyl]-1,2-dihydro-3H-benz[e]indole or a physiologically functional derivative thereof.

* * * * *